US012685513B2

(12) United States Patent (10) Patent No.: US 12,685,513 B2
Kameda et al. (45) Date of Patent: Jul. 21, 2026

(54) ULTRASOUND DIAGNOSTIC APPARATUS, ULTRASONIC IMAGING METHOD, AND STORAGE MEDIUM

(71) Applicant: KONICA MINOLTA, INC., Tokyo (JP)

(72) Inventors: Masanobu Kameda, Kokubunji (JP); Morio Nishigaki, Fujisawa (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

(21) Appl. No.: 18/955,712

(22) Filed: Nov. 21, 2024

(65) Prior Publication Data

US 2025/0176943 A1 Jun. 5, 2025

(30) Foreign Application Priority Data

Nov. 30, 2023 (JP) ................................. 2023-202295

(51) Int. Cl.
*A61B 8/00* (2006.01)
*A61B 8/08* (2006.01)

(52) U.S. Cl.
CPC ................ *A61B 8/48* (2013.01); *A61B 8/461* (2013.01)

(58) Field of Classification Search
CPC ......... A61B 8/48; A61B 8/461; A61B 8/4405; A61B 8/5223; A61B 8/5246; A61B 8/54; A61B 8/488; A61B 8/06
See application file for complete search history.

(56) References Cited

U.S. PATENT DOCUMENTS

2008/0269610 A1* 10/2008 Burla ..................... G01S 7/5205
600/447
2009/0076384 A1* 3/2009 Saad ................... G01S 7/52098
600/437

FOREIGN PATENT DOCUMENTS

CN        117038020 A * 11/2023 ............. G16H 30/00
JP         3411732 B2    6/2003
JP        2015-116331 A    6/2015
JP        2018061659 A * 4/2018

OTHER PUBLICATIONS

The JP-2018061659-A machine translation (Year: 2018).*
The CN-117038020-A machine translation (Year: 2023).*

* cited by examiner

*Primary Examiner* — Alexei Bykhovski
(74) *Attorney, Agent, or Firm* — Boone IP Law

(57) ABSTRACT

Provided is an ultrasound diagnostic apparatus comprising a hardware processor. The hardware processor sequentially performs ultrasonic imaging of a first patient in each of a plurality of routines by controlling an imager which generates ultrasonic image data by ultrasonic imaging of a subject of a patient based on information on a routine set including the plurality of routines of ultrasound imaging using a parameter, and when a parameter of a selected one of the plurality of routines is modified, the hardware processor changes a parameter of one or more routines on downstream of the selected one of the plurality of routines according to the modified parameter.

13 Claims, 9 Drawing Sheets

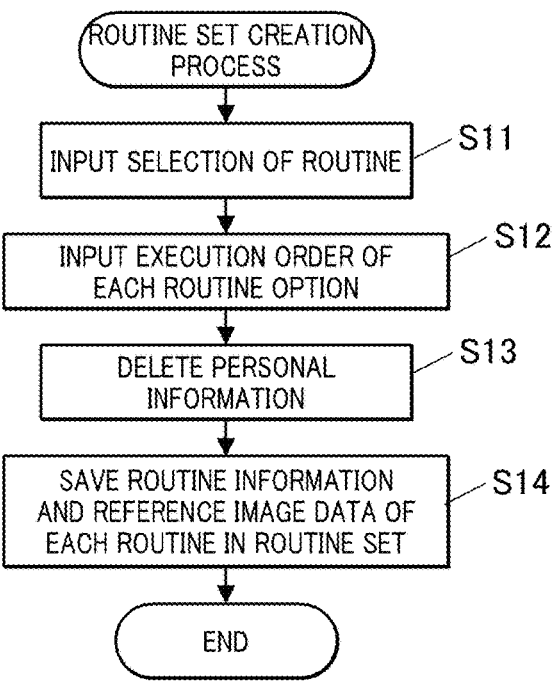

ROUTINE SET CREATION PROCESS

INPUT SELECTION OF ROUTINE — S11

INPUT EXECUTION ORDER OF EACH ROUTINE OPTION — S12

DELETE PERSONAL INFORMATION — S13

SAVE ROUTINE INFORMATION AND REFERENCE IMAGE DATA OF EACH ROUTINE IN ROUTINE SET — S14

END

FIG. 4

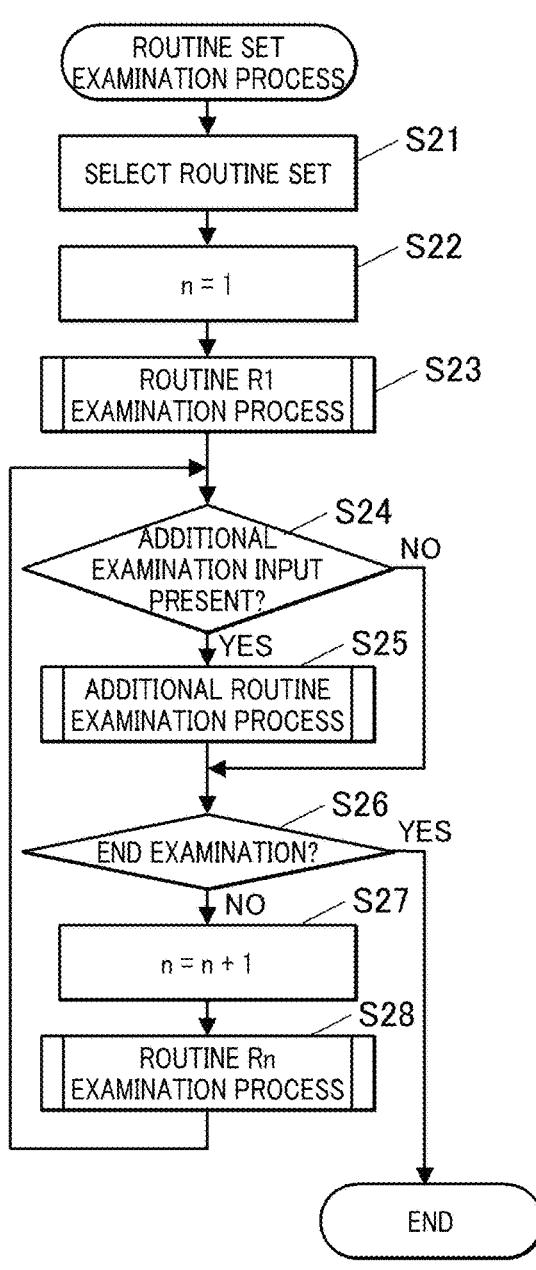

ROUTINE SET EXAMINATION PROCESS

SELECT ROUTINE SET — S21

$n = 1$ — S22

ROUTINE R1 EXAMINATION PROCESS — S23

ADDITIONAL EXAMINATION INPUT PRESENT? — S24     NO

YES — S25

ADDITIONAL ROUTINE EXAMINATION PROCESS

END EXAMINATION? — S26     YES

NO — S27

$n = n + 1$

ROUTINE Rn EXAMINATION PROCESS — S28

END

FIG. 7

ROUTINE Rn EXAMINATION PROCESS

READ OUT
ROUTINE INFORMATION OF ROUTINE Rn
AND REFERENCE IMAGE DATA — S61

REFLECT
UPSTREAM MODIFICATION
PARAMETERS? — S62
NO

YES — S63

CHANGE PARAMETERS

DISPLAY AND SET
ROUTINE INFORMATION — S64

DISPLAY
REFERENCE IMAGE? — S65
NO

YES — S66

DISPLAY REFERENCE IMAGE DATA

MODIFICATION INPUT
PRESENT? — S67
NO

YES — S68

SET MODIFIED PARAMETERS

EXECUTE IMAGING OF ROUTINE Rn — S69

SAVE ROUTINE INFORMATION,
MODIFIED PARAMETERS,
AND ULTRASOUND IMAGE DATA — S70

RETURN

FIG. 8

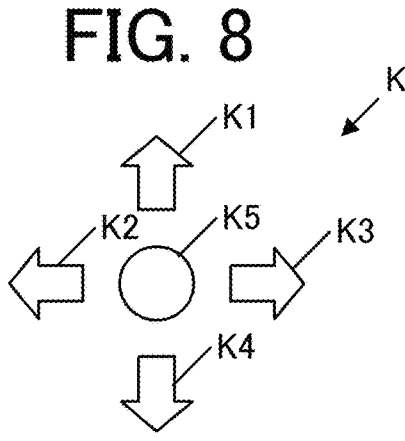

K

K1

K2    K5    K3

K4

ULTRASOUND DIAGNOSTIC APPARATUS, ULTRASONIC IMAGING METHOD, AND STORAGE MEDIUM

CROSS-REFERENCE TO RELATED APPLICATIONS

This application is based upon and claims the benefit of priority from the prior Japanese Patent Application No. 2023-202295, filed on Nov. 30, 2024, the entire contents of which are incorporated herein by reference.

BACKGROUND OF THE INVENTION

Technical Field

The present invention relates to an ultrasound diagnostic apparatus, an ultrasonic imaging method, and a storage medium.

Background Art

There has been conventionally known an ultrasound diagnostic apparatus that emits ultrasonic waves with an ultrasound probe to the interior of a subject, receives the reflected waves, and analyzes the reflected waves to display an ultrasonic image of the interior of the subject. The subject is a living body of a patient or the like.

In ultrasound diagnosis (examination), an examination method is known in which a plurality of types of ultrasonic images are captured by sequentially executing a series of examination steps. For example, an ultrasonic examination system is known in which a series of inspection protocols (examination processes) are created by arranging a plurality of images obtained by operations of a plurality of pieces of operation information (see Japanese Unexamined Patent Publication No. 2018-61659).

Further, there is known an ultrasound diagnostic apparatus that generates a series of examination protocols (examination procedures) by performing machine learning on an operation history and examination contents executed by the operation (see Japanese Unexamined Patent Publication No. 2015-116331).

There is also known an ultrasound diagnostic apparatus that automatically operates according to a registered sequence of a series of operations (examination steps) and temporarily stops according to a command operation during the execution (refer to Japanese Patent No. 3411732). This ultrasound diagnostic apparatus performs a desired action (examination process) by an operation during the temporary stop, and releases the temporary stop by a command operation.

SUMMARY OF THE INVENTION

The examination protocol and sequence described in Japanese Unexamined Patent Publication No. 2018-61659, Japanese Unexamined Patent Publication No. 2015-116331, and Japanese Patent No. 3411732 are examination processes of ultrasonic imaging (image capturing) corresponding to the operation contents. However, the optimum parameter setting for ultrasonic imaging in each step varies depending on individual differences among patients. If a patient has been previously examined, parameters in the previous examination may be used. However, it is efficient for the examiner to proceed with an examination of a new patient using a typical example (template) of a parameter set in a routine or using a parameter set of another patient who is considered to be close to the concerning patient. However, when a template or a parameter set for another patient is used, the values of the parameters do not completely match the new patient. Therefore, it is necessary to adjust parameters in each examination process. Furthermore, in execution of a series of examination steps (routine set), parameter setting which is common in one routine and in a downstream routine may be performed. Also in this case, it is necessary to adjust the same parameters in each routine. Therefore, a burden on an examiner such as a doctor is large.

An object of the present invention is to reduce the burden of parameter setting on the examiner in an ultrasonic imaging examination using a routine set.

To achieve at least one of the abovementioned objects, according to an aspect of the present disclosure, an ultrasound diagnostic apparatus includes:

a hardware processor, wherein the hardware processor sequentially performs ultrasonic imaging of a first patient in each of a plurality of routines by controlling an imager which generates ultrasonic image data by ultrasonic imaging of a subject of a patient based on information on a routine set including the plurality of routines of ultrasound imaging using a parameter, and when a parameter of a selected one of the plurality of routines is modified, the hardware processor changes a parameter of one or more routines on downstream of the selected one of the plurality of routines according to the modified parameter.

To achieve at least one of the abovementioned objects, according to another aspect of the present disclosure, an ultrasonic imaging method includes:

sequentially performing ultrasonic imaging of a first patient in each of a plurality of routines by control of an imager which generates ultrasonic image data by the ultrasonic imaging of a subject of a patient based on information on a routine set including the plurality of routines of ultrasound imaging using a parameter; and changing, when a parameter of a selected one of the plurality of routines is modified, a parameter of one or more routines on downstream of the selected one of the plurality of routines according to the modified parameter.

To achieve at least one of the abovementioned objects, according to another aspect of the present disclosure, a storage medium stores a program that causes a computer to:

sequentially perform ultrasonic imaging of a first patient in each of a plurality of routines by control of an imager which generates ultrasonic image data by the ultrasonic imaging of a subject of a patient based on information on a routine set including the plurality of routines of ultrasound imaging using a parameter; and change, when a parameter of a selected one of the plurality of routines is modified, a parameter of one or more routines on downstream of the selected one of the plurality of routines according to the modified parameter.

According to the present invention, it is possible to reduce the burden of parameter setting on an inspector in inspection of ultrasonic imaging by routine setting.

BRIEF DESCRIPTION OF THE DRAWINGS

The accompanying drawings are not intended as a definition of the limits of the invention but illustrate embodiments of the invention, and together with the general description given above and the detailed description of the embodiments given below, serve to explain the principles of the invention, wherein:

FIG. 2 is a block diagram showing a functional configuration of the ultrasound diagnostic apparatus;

FIG. 3 is a flowchart showing a routine set creation process;

FIG. 4 is a flowchart showing a routine set examination process;

FIG. 7 is a flowchart showing a routine examination process;

FIG. 8 shows a key group;

DESCRIPTION OF EMBODIMENTS

Hereinafter, one or more embodiments of the present invention will be described with reference to the drawings. However, the scope of the present invention is not limited to the disclosed embodiments.

Figure 1:
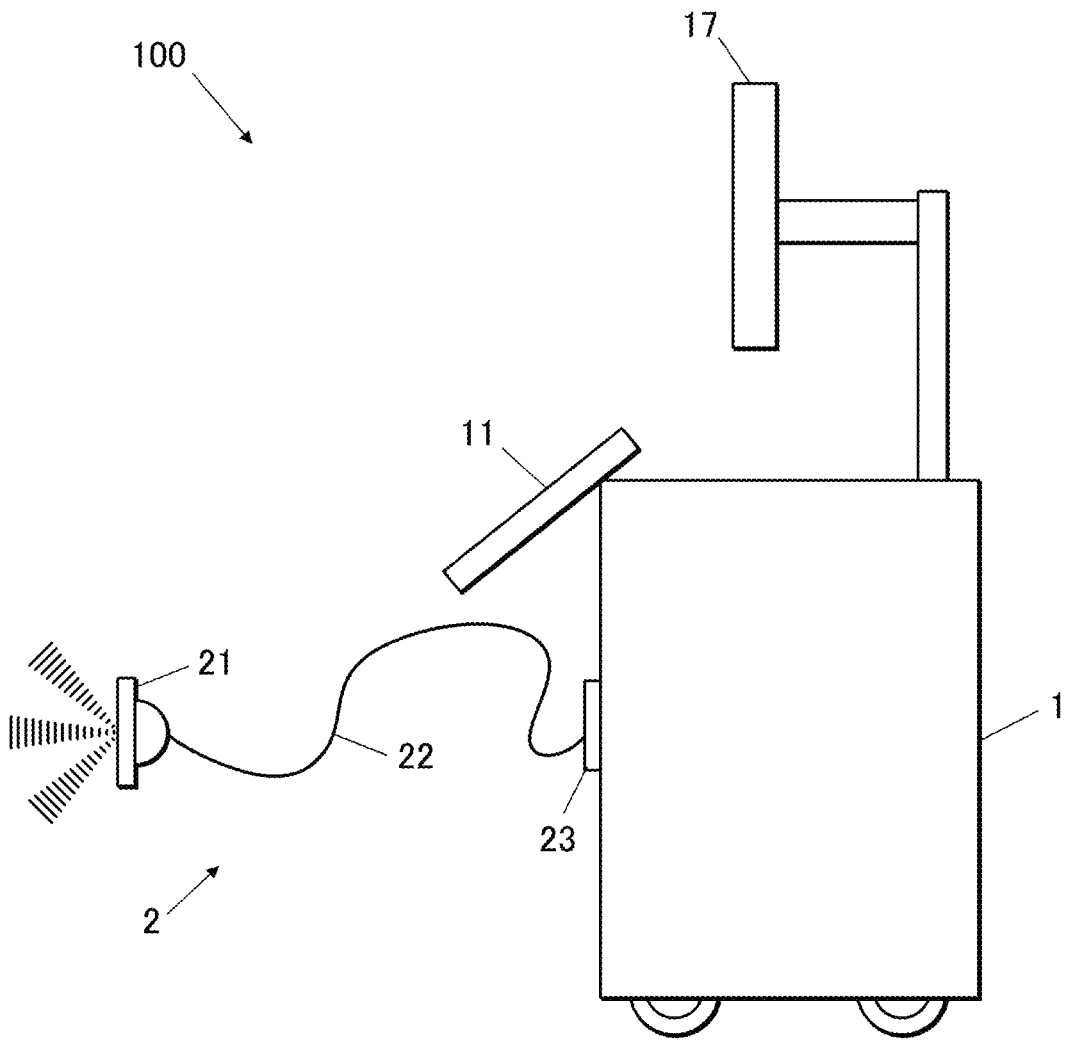
FIG. 1 is a schematic diagram of an ultrasound diagnostic apparatus according to an embodiment of the present invention.
Figure 2:
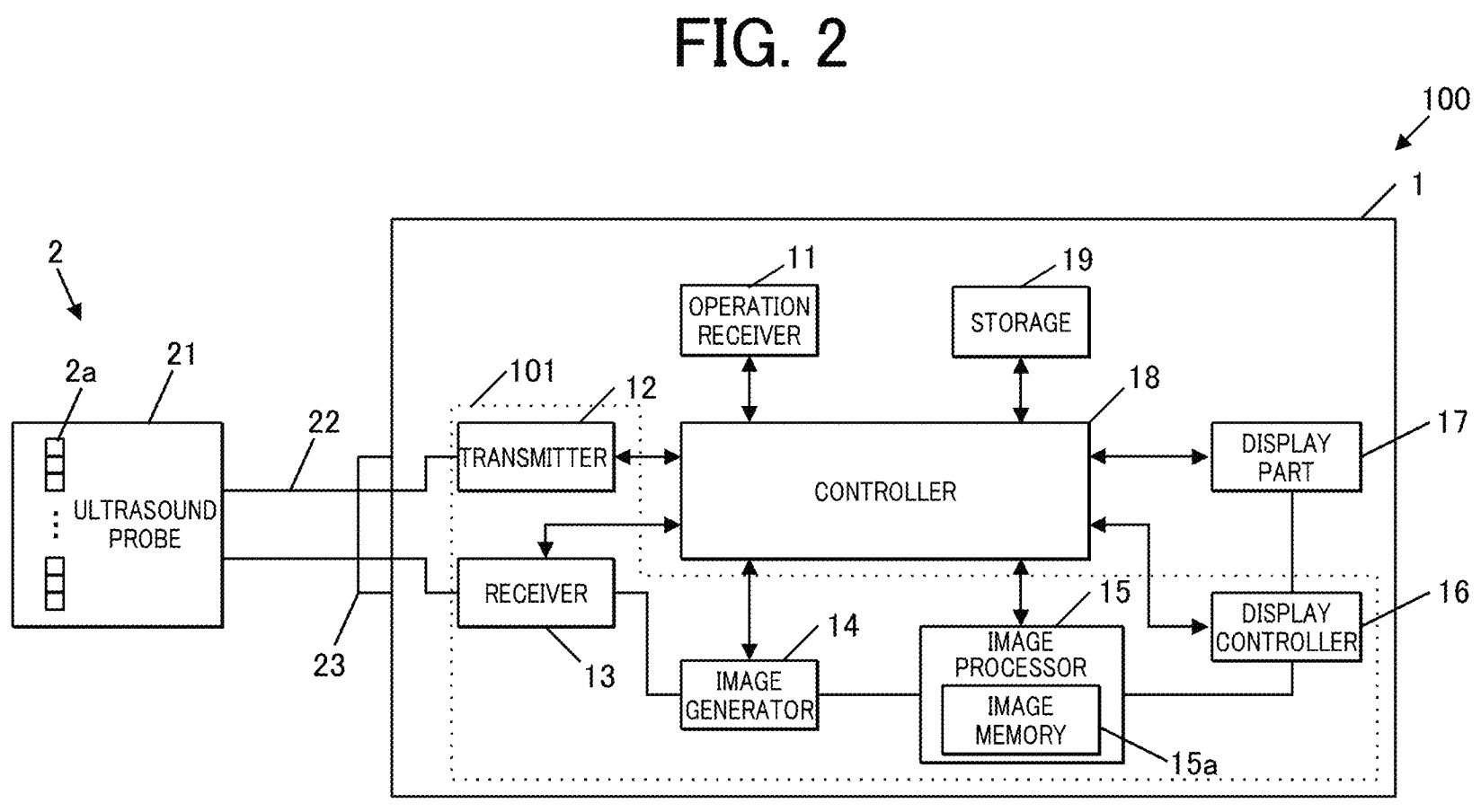

First, an apparatus configuration according to the present embodiment will be described with reference to FIGS. 1 and 2. FIG. 1 is a schematic diagram of an ultrasound diagnostic apparatus 100 according to the present embodiment. FIG. 2 is a block diagram showing a functional configuration of the ultrasound diagnostic apparatus 100.

As shown in FIG. 1, the ultrasound diagnostic apparatus 100 is provided in a medical facility such as a hospital, and generates ultrasonic image data by emitting ultrasonic waves to a subject such as a living body of a patient.

As shown in FIG. 2, the ultrasound diagnostic apparatus 100 includes an ultrasound diagnostic apparatus main body 1 and an ultrasound probe 2. The ultrasound probe 2 is connected to the ultrasound diagnostic apparatus main body 1. The ultrasound probe 2 transmits ultrasonic waves (transmitted ultrasonic waves) into a subject and receives ultrasonic waves reflected inside the subject (reflected ultrasonic waves: echoes). The ultrasound probe 2 has an ultrasound probe main body 21, a cable 22, and a connector 23. The ultrasound probe main body 21 is a header of the ultrasound probe 2, which transmits and receives ultrasonic waves. The cable 22 is connected to the ultrasound probe main body 21 and the connector 23. The cable 22 is a cable through which a driving signal for the ultrasound probe main body 21 and a reception signal of ultrasonic waves flow. The connector 23 is a plug connector for establishing a connection with a receptacle connector (not illustrated) of the ultrasound diagnostic apparatus main body 1.

The ultrasound diagnostic apparatus main body 1 is connected to the ultrasound probe main body 21 via the connector 23 and the cable 22. The ultrasound diagnostic apparatus main body 1 transmits a driving signal, which is an electric signal, to the ultrasound probe main body 21 to direct the ultrasound probe main body 21 to transmit transmission ultrasonic waves to the subject. The ultrasound probe 2 generates a reception signal, which is an electric signal, according to the reflected ultrasonic waves from the inside of the subject received by the ultrasound probe main body 21. The ultrasound diagnostic apparatus main body 1 images the internal state of the subject as ultrasonic image data on the basis of the reception signal generated by the ultrasound probe 2.

The ultrasound probe main body 21 has transducers 2a (FIG. 2) at a distal end side. For example, the transducers 2a are arranged in a one dimensional array in the scanning direction (azimuth direction). Alternatively, the transducers 2a may be arranged in a two-dimensional array. In the present embodiment, the ultrasound probe 2 is a linear scanning type electronic scanning probe. However, the ultrasound probe 2 may be of either an electronic scanning type or a mechanical scanning type. In addition, the ultrasound probe 2 may be of any of a linear scanning type, a sector scanning type, and a convex scanning type. The ultrasound diagnostic apparatus main body 1 and the ultrasound probe 2 may be configured to perform wireless communication between each other instead of wired communication via the cable 22. The wireless communication is an ultra-wide band (UWB), for example.

The operation receiver 11 is a control panel or the like that receives various operation inputs from an inspector such as a doctor or a technician. The operation receiver 11 includes operational elements, such as a push button, an encoder, a lever switch, a joystick, a trackball, a keyboard, a touch pad, and/or a multifunction switch.

The display part 17 includes a display panel such as a liquid crystal display (LCD), an organic electro-luminescence (EL) display, or an inorganic EL display. The display part 17 displays display information such as ultrasonic image data on the display panel.

As shown in FIG. 2, the ultrasound diagnostic apparatus main body 1 includes an operation receiver 11, a transmitter 12, a receiver 13, an image generator 14, an image processor 15, a display controller 16, a display part 17, a controller (hardware processor) 18, and a storage 19. The transmitter 12, the receiver 13, the image generator 14, the image processor 15, and the display controller 16 function as an imager 101 that generates ultrasonic image data by ultrasonic imaging on a subject of a patient.

The operation receiver 11 receives various operation inputs from an examiner and outputs the operation signals to the controller 18. The operation receiver 11 may include a touch screen formed integrally with the display screen of the display part 17 and configured to receive touch inputs by the examiner.

Under the control of the controller 18, the transmitter 12 supplies a driving signal, which is an electric signal, to the ultrasound probe 2 to direct the ultrasound probe 2 to generate transmission ultrasonic waves. The transmitter 12 includes, for example, a clock generation circuit, a delay circuit, and a pulse generation circuit. The clock generation circuit generates a clock signal for determining the transmission timing and transmission frequency of the driving signal. The delay circuit sets a delay time for each individual path corresponding to each transducer 2a and delays the transmission of the driving signal by the set delay time. The delay circuit focuses transmission beams formed by the transmission ultrasonic waves by the delay. The pulse generating circuit generates a pulse signal as a driving signal at a predetermined cycle. The transmitter 12 drives, for example, a consecutive part (e.g., 64) of the plurality of (e.g., 192) transducers 2a arrayed in the ultrasound probe 2 to generate transmission ultrasonic waves. Then, the transmitter 12 performs scanning by shifting the driven transducer 2a in the scanning direction each time the transmission ultrasound is generated.

The receiver 13 receives a reception signal, which is an electric signal, from the ultrasound probe 2 under the control of the controller 18. The receiver 13 includes, for example, an amplifier, an analog to digital (A/D) conversion circuit, and a phasing addition circuit. The amplifier amplifies the reception signal with a preset amplification factor for each individual path corresponding to each of the transducers 2a. The A/D conversion circuit performs analog/digital conversion on the amplified reception signal. The phasing addition circuit applies, to the A/D converted reception signals, delay times determined for the respective individual paths corresponding to the respective transducers 2a, thereby adjusting the time phase. After the above processes, the phasing addition circuit generates sound ray data by adding up the reception signals (phasing addition).

Under the control of the controller 18, the image generator 14 performs envelop detection processing, logarithmic compression, and so forth on the sound ray data generated by the receiver 13. After the above processes, the image generator 14 further adjusts the dynamic range and the gain of the sound ray data to convert the data into brightness. Through the brightness conversion, the image generator 14 generates B (brightness)-mode image data including pixels having brightness values as received energy. That is, the B-mode image data represents an intensity of a reception signal by a brightness. Here, a configuration in which the ultrasound diagnostic apparatus 100 generates and displays B-mode image data as tomographic images will be described. The image generator 14 may be configured to generate image data in any image mode other than the B mode, such as a pulse Doppler mode and a color Doppler mode, as an image mode. The pulse Doppler mode is an image mode in which values such as a velocity of a blood flow between Doppler gates in a tomographic image is displayed in a graph. The color Doppler (color flow) mode is an image mode in which a tomographic image on which the velocity, direction, power, dispersion, and the like of the blood flow of the subject are color-mapped is superimposed on the B-mode image data and displayed.

The image processor 15 includes an image memory 15a. The image memory 15a is constituted of a semiconductor memory, such as a dynamic random access memory (DRAM), for example. The image processor 15 stores the B-mode image data transmitted from the image generator 14 in the image memory 15a in units of frames under the control of the controller 18. The B-mode image data in units of frames may be referred to as ultrasonic image data. The image processor 15 transmits the ultrasonic image data stored in the image memory 15a to the display controller 16 frame by frame at predetermined time intervals under the control of the controller 18.

The display controller 16 is, for example, a digital scan converter (DSC). Under the control of the controller 18, the display controller 16 performs processing of coordinate conversion or the like on the B-mode image data inputted from the image processor 15 to convert this data into an image signal for display. The display controller 16 outputs the image signal to the display part 17.

Under the control of the controller 18, the display part 17 displays an ultrasonic image on the display panel in accordance with the image signal outputted from the display controller 16. Furthermore, the display part 17 displays various display information inputted from the controller 18 on the display panel.

The controller 18 includes, for example, a central processing unit (CPU), a read only memory (ROM), and a random access memory (RAM). The controller 18 reads various processing programs stored in the ROM, develops them in the RAM, and controls the units of the ultrasound diagnostic apparatus 100 by cooperation between the developed programs and the CPU. The ROM includes a nonvolatile memory such as a semiconductor. The ROM stores a system program corresponding to the ultrasound diagnostic apparatus 100, various processing programs executable on the system program, various data such as a gamma table, and the like. In particular, the ROM stores a routine set creation program for executing a routine set creation process, which will be described later, and a routine set examination program for executing a routine set examination process. These programs are stored in the RAM in the form of computer-readable program codes. The CPU sequentially executes operations according to the program codes on the RAM. The RAM forms a work area in which various programs executed by the CPU and data related to these programs are temporarily stored.

The storage 19 is a storage unit such as a hard disk drive (HDD), a solid state drive (SSD) or the like that stores information such as ultrasonic image data in a writable and readable manner.

Figure 5:
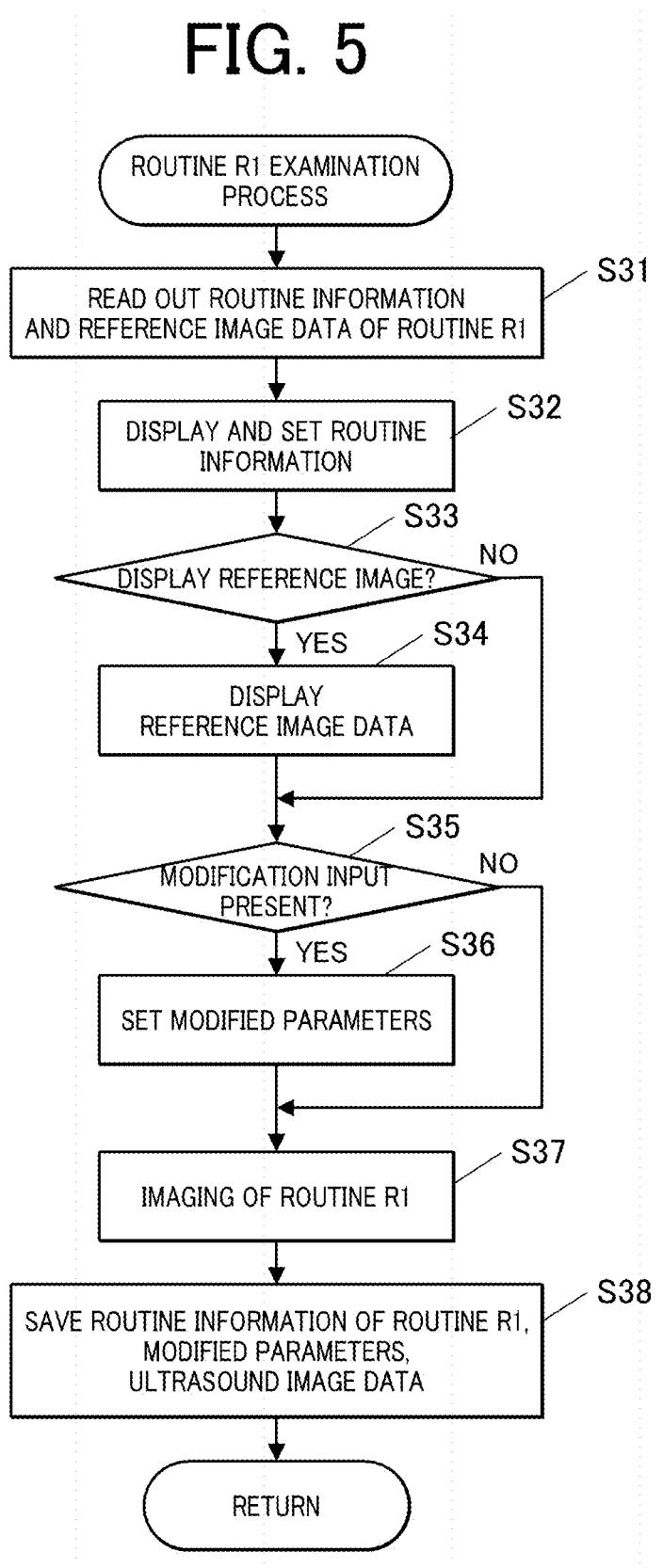
FIG. 5 is a flowchart showing a routine examination process.
Figure 6:
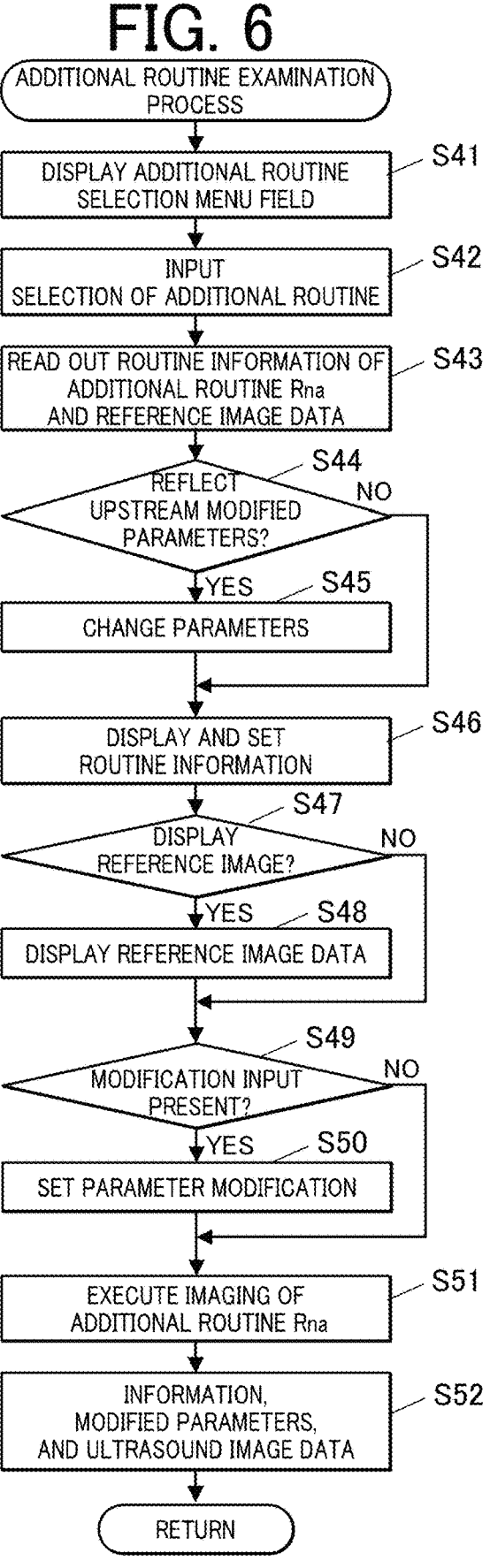
FIG. 6 is a flowchart showing an additional routine examination process.
Figure 9:
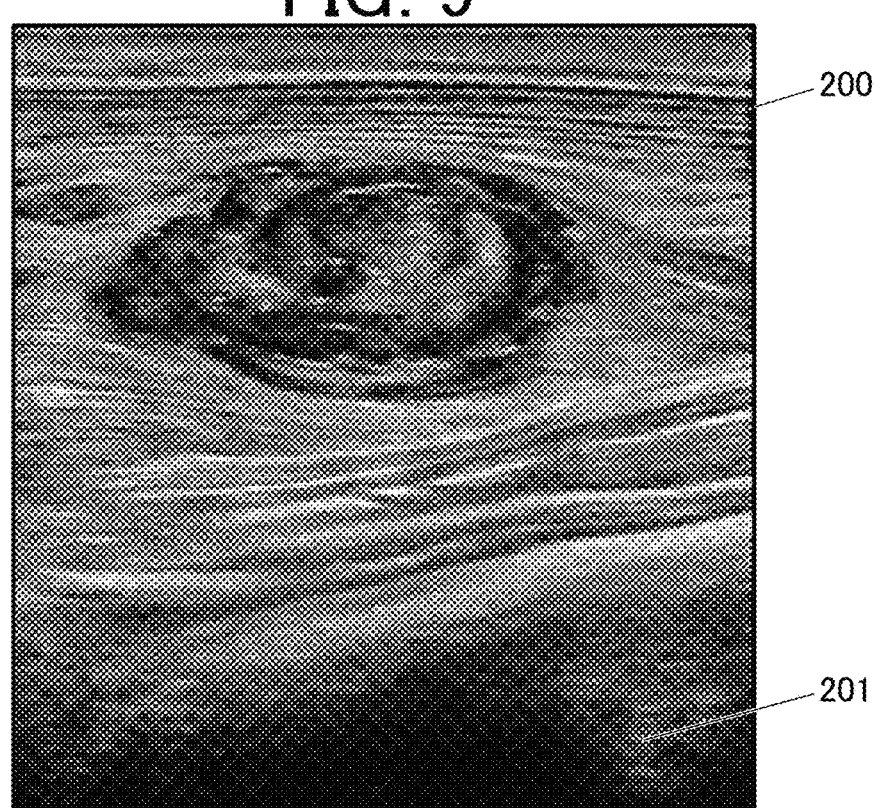
FIG. 9 shows an ultrasonic image being captured.
Figure 10:
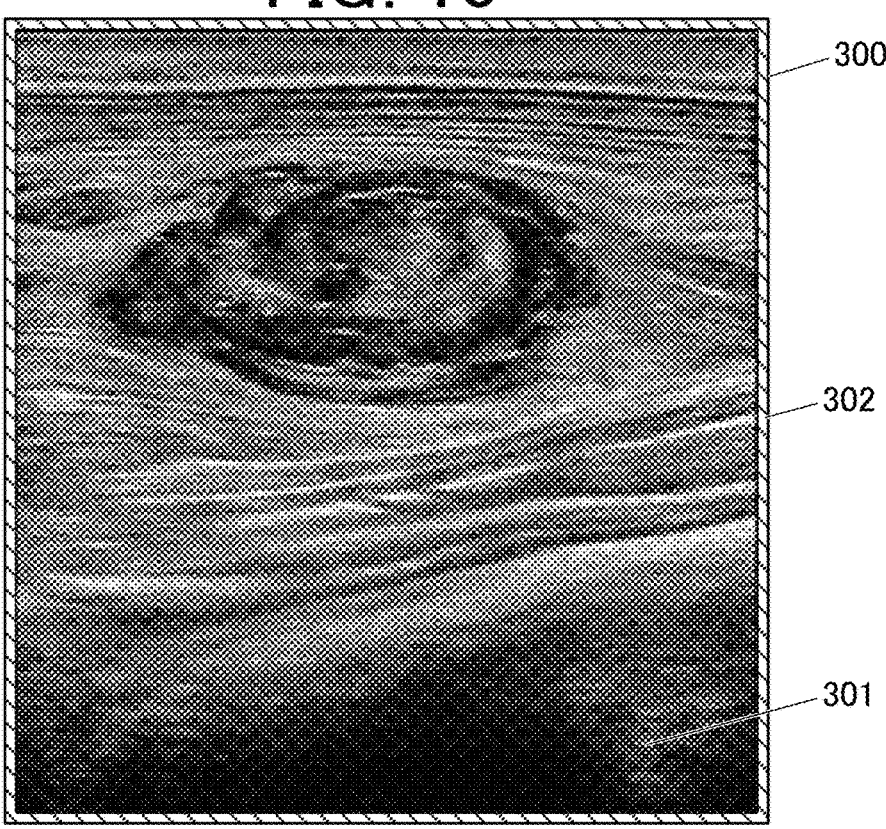
FIG. 10 shows a ultrasonic image in the past.
Figure 11:
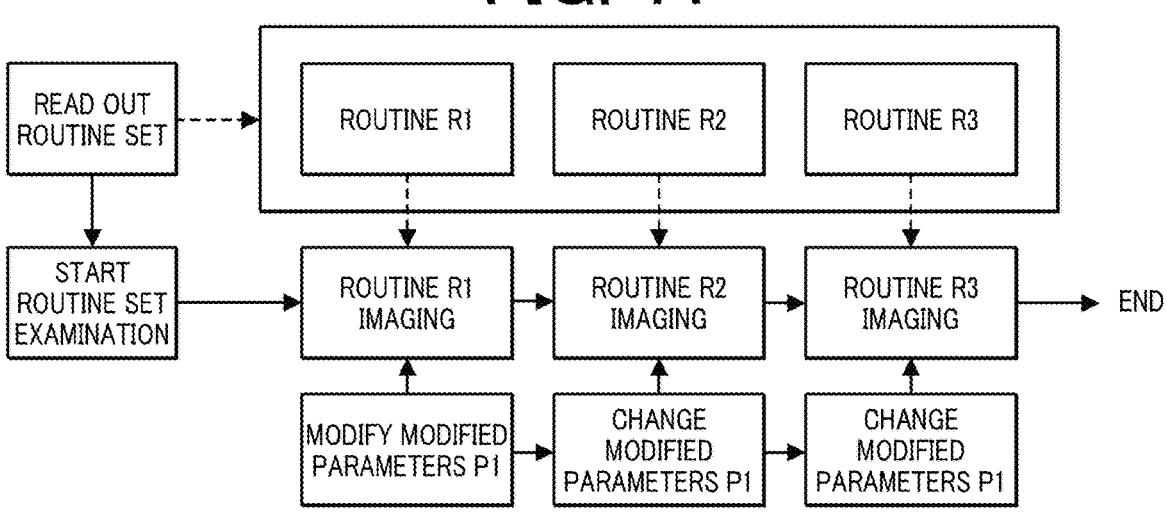
FIG. 11 shows an example of a routine set and a parameter change.

With reference to FIGS. 3 to 12, operations of the ultrasound diagnostic apparatus 100 according to the present embodiment will be described. FIG. 3 is a flowchart showing a routine set creation process. FIG. 4 is a flowchart showing a routine set examination process. FIG. 5 is a flowchart of a routine R1 examination process. FIG. 6 is a flowchart showing an additional routine examination process. FIG. 7 is a flowchart showing a routine Rn examination process. FIG. 8 shows a key group K. FIG. 9 shows an ultrasonic image 200 being captured. FIG. 10 shows an ultrasonic image 300 in the past. FIG. 11 shows an example of a routine set and parameter change. FIG. 12A shows an additional routine selection menu field M. FIG. 12B shows an example of a routine set, parameter change, and routine addition.

First, the routine set creation process executed by the ultrasound diagnostic apparatus 100 will be described with reference to FIG. 3. The routine set creation process is creating a routine set including a plurality of routines as a series of examination processes for ultrasonic imaging using the ultrasound diagnostic apparatus 100.

In the ultrasound diagnostic apparatus 100, a routine set examination process described later and examinations in individual examination steps have been executed in advance for a patient(s) as an examination subject(s) in the past. Routine information such as an image mode and parameters used in each routine of the routine set executed for examination and the acquired ultrasonic image data are stored in the storage 19. In addition, the information such as the image mode and parameters used in the examination steps individually executed and the acquired ultrasonic image data are also stored in the storage 19. Information obtained in each examination step is also referred to as routine information for convenience of description. In each routine, the routine information and the ultrasonic image data are associated with each other. The routine information includes personal information of an examined patient. In addition, the ultrasonic image data includes personal information of the examined patient in the image or tag information. The personal information is information by which an individual patient to be examined can be identified.

The parameters according to the present embodiment are information on conditions for ultrasonic imaging, and are various parameters to be set in the imager 101. When the image mode is the B mode, the parameters include a dynamic range, on/off of harmonics, and a field of view (FOV). The FOV is an effective field of view, and is a maximum display depth of a tomographic image in an ultrasound examination. When the image mode is the pulse Doppler mode, the parameters are a Doppler gate width, deflection angle correction, Doppler gate position, and the like. In a case where the image mode is the color Doppler mode, the parameters are information such as switching of display information of the blood flow velocity, dispersion, and the like. The parameters common to all the image modes are a transmission voltage, a transmission/reception frequency, a reception gain, and the like. The parameters common to all the blood flow image modes are a flow velocity range, a filter coefficient of a clutter removing filter, and the like.

In the ultrasound diagnostic apparatus 100, for example, an instruction to execute the routine set creation process is input by the examiner via the operation receiver 11. Triggered by the execution instruction, the controller 18 executes the routine set creation process in accordance with the routine set creation program stored in the ROM.

As shown in FIG. 3, the controller 18 displays the routine information and the ultrasonic image data stored in the storage 19 as routine options on the display part 17 (Step S11). In Step S11, the controller 18 receives, from the examiner via the operation receiver 11, a selection input of a plurality of routine options constituting a new routine set.

The controller 18 receives an input of an execution order of the routine options selected in Step S11 from the examiner via the operation receiver 11 (Step S12). This execution order is an execution order of the respective routine options in the new routine set.

The controller 18 deletes the individual information of the patient from the routine information and the ultrasonic image data of the routine options selected in Step S11 (Step S13). For example, the text information of the personal information in the routine information and the personal information in the image of the ultrasonic image data and the tag information are deleted.

The controller 18 stores, in the storage 19, the routine information of each routine from which the individual information has been deleted in Step S13 and the ultrasonic image data (Step S14). The routine information of each routine and the ultrasonic image data are stored as the routine information and the reference image data of each routine of a new routine set. Each piece of data is stored in association with identification information (name) of the new routine set. The routine set creation process ends.

Next, with reference to FIGS. 4 to 12, the routine set examination process executed by the ultrasound diagnostic apparatus 100 will be described. The routine set examination process is sequentially performing examinations of ultrasonic imaging in a series of routines on the basis of parameters and reference image data of a selected routine set.

In the ultrasound diagnostic apparatus 100, for example, an instruction to execute the routine set examination process is input by the examiner via the operation receiver 11. Triggered by the execution instruction, the controller 18 executes the routine set examination process in accordance with the routine set examination program stored in the ROM.

As shown in FIG. 3, the controller 18 displays, on the display part 17, a list of the names of the routine sets stored in the storage 19 (Step S21). In Step S21, the controller 18 receives an input of selection of a routine set to be executed from the examiner via the operation receiver 11. The controller 18 substitutes 1 for a variable n of the execution order of the routines in the selected routine set (Step S22). The controller 18 executes routine R1 examination process for the first routine R1 in the execution order of the selected routine set (Step S23).

Here, the routine R1 inspection processing of Step S23 will be described with reference to FIG. 5. First, the controller 18 reads, from the storage 19, the routine information and the reference image data of Routine R1 that is the first in the execution order (Step S31). The controller 18 displays the routine information read in Step S31 on the display part 17, and sets the image mode and parameters for ultrasonic imaging (Step S32).

The controller 18 determines whether or not to display a reference image of the routine R1 based on the input by the examiner via the operation receiver 11 (Step S33). In Step S33, for example, the key group K shown in FIG. 8 is displayed on the display part 17. The key group K includes, as software keys, directional keys including an up direction key K1, a left direction key K2, a right direction key K3, and a down direction key K4, and a click key K5. The up direction key K1 and the down direction key K4 function as first operation elements. The click key K5 function as a second operation element.

The up direction key K1 receives, for example, an input of an instruction to display the reference image. The left direction key K2 receives, for example, a click input of an instruction to return to the previous routine in the execution order. The right direction key K3 receives, for example, a click input of an instruction for transition to the next routine in the execution order. The down direction key K4 receives, for example, a click input of an instruction for transition to the current examination (imaging, parameter setting). The click key K5 receives, for example, a click input of an instruction to add a new routine to the current routine set. That is, in Step S33, it is determined whether or not to display the reference image of the routine K1 according to whether or not the up direction key R1 is clicked.

The operation elements of the key group described above are not limited to the example of the key group K in FIG. 8. For example, the keys K1 to K4 are not limited to the directional keys, and may be, for example, a menu field including a menu of each operation input content. The key group K may not include the click key K5 and an input of an instruction to add a new routine is accepted by, for example, pressing and holding the down key K4 for a predetermined time or longer. The operation elements of the key group may not be software keys, and operation elements corresponding to the key group K may be provided as hardware keys in the operation receiver 11.

If the reference image is to be displayed (YES in Step S33), the controller 18 displays the reference image read in Step S31 on the display part 17 (Step S34). An ultrasonic image of the patient under examination, which is captured in Routine R1 in Step S37, is displayed as, for example, a B-mode ultrasonic image 200 shown in FIG. 9. The ultrasonic image 200 includes only an ultrasonic image main body 201. Reference image data of the patient under examination or another patient in Step S34 is displayed, for example, as a B-mode ultrasonic image 300 shown in FIG. 10. The ultrasonic image 300 includes an ultrasonic image main body 301 and a frame 302. The frame 302 is, for example, a red frame arranged around the ultrasonic image main body 301 in order to distinguish the ultrasonic image 300 from the ultrasonic image 200. However, the display mode for identifying the ultrasonic image 300 from the ultrasonic image 200 is not limited to the frame 302. For example, red characters "reference image" may be placed in the vicinity of the ultrasonic image main body 301 as a display mode. The color of the display mode is not limited to red.

Back in FIG. 5, after Step S34 is executed or when a reference image is not to be displayed (Step S33; NO), the process proceeds to Step S35. The controller 18 receives an input of modification of the parameter set in Step S32 from the examiner via the operation receiver 11 (Step S35). In Step S35, the controller 18 determines whether or not there is a parameter modification input. The input of parameter modification includes the transition to the parameter modification process (mode) by a click input of the down direction key K4 and the input of the modified parameter through the operation receiver 11.

The display position of the reference image (e.g., the ultrasonic image 300) in Step S34 may be on an ultrasonic image (e.g., the ultrasonic image 200) in Step S37 described later. In this configuration, when Step S35 is executed, for example, the down direction key K4 is clicked as appropriate, and the reference image is hidden. However, the configuration is not limited to this. The display position of the reference image in Step S34 may be different from the display position of the ultrasonic image in Step S37. For example, the reference image of Step S34 and the ultrasonic image of Step S37 are displayed in parallel. In this case, the reference image in Step S34 may be kept displayed until Step S37.

When there is a parameter modification input (Step S35; YES), the controller 18 sets the modified parameters input in Step S35 for ultrasonic imaging (Step S36). After executing Step S36 or when there is no input of parameter modification (Step S35; NO), the process proceeds to Step S37. Based on the image mode and the parameters set in Steps S32 and S36, the controller 18 controls the imager 101 to perform ultrasonic imaging of the subject (Step S37). In Step S37, ultrasonic image data of a subject is generated. As shown in the ultrasonic image 200 of FIG. 9, the generated ultrasonic image is displayed on the display part 17 as the ultrasonic image of the routine R1.

The controller 18 stores the routine information of the routine R1, the modified parameter of Step S36, and the ultrasonic image data of Step S37 in the storage 19 in association with each other (Step S38). Each piece of data is stored in association with identification information (name) of the routine R1. The modified parameters are saved when Step S36 is executed. The routine R1 examination process ends.

Back in FIG. 4, the controller 18 accepts an additional examination input from the examiner via the operation receiver 11, and determines whether or not there is an additional examination input (Step S24). The additional examination is an examination of a routine to be newly added immediately after the already executed routine in the routine set. In Step S24, an additional examination input is received, for example, by a click input of the click key K5 of the key group K.

When there is an additional examination input (Step S24; YES), the controller 18 executes an additional routine examination process to perform the examination of the additional routine (Step S25). Here, the additional routine examination process of Step S25 will be described with reference to FIG. 6. First, the controller 18 displays an additional routine selection menu field on the display part 17 (Step S41). The additional routine selection menu field is a menu field in which identification information such as the name of the routine corresponding to the routine information stored in the storage 19 is selectably displayed. The additional routine selection menu field displays, for example, identification information of a routine other than each routine of the selected routine set. However, the present invention is not limited to this. The additional routine selection menu field may display, for example, identification information of routines including each routine of the routine set being selected.

The controller 18 accepts an input of selection of an additional routine in the additional routine selection menu field from the examiner via the operation receiver 11 (Step S42). The controller 18 reads, from the storage 19, the routine information and the reference image data of the additional routine selected in Step S42 (Step S43). This additional routine is added immediately after execution of the n-th routine Rn in the execution order, and is hereinafter referred to as the additional routine Rna.

The controller 18 determines whether to reflect, in the additional routine Rna, the modified parameters of a routine on the upstream from the additional routine Rna of the selected routine set (Step S44). In step S44, for example, the upstream routine information and the modified parameters in the storage 19 are referred to. In a case where a parameter common to the additional routine Rna is in the modified parameters of the upstream routine, the controller 18 reflects it in Step S44.

In addition, the controller 18 may not reflect it in Step S44. For example, consider a case where the image mode is the color Doppler mode. The cut-off frequency of the clutter removing filter when the blood flow of the heart is observed is to be increased. At this time, in many cases, it is not necessary to change the filter setting when the blood flow of the liver of the routine on the downstream of the same routine set is observed. Such modified parameters are not reflected on the routines on the downstream. The determination may be made by receiving an input of whether or not to reflect the modified parameter of the upstream routine on the additional routine Rna from the examiner via the operation receiver 11.

When the modified parameter is to be reflected (Step S44; YES), the process proceeds to Step S45. The controller 18 reads the modified parameter for the upstream routines from the storage 19 (Step S45). In Step S45, the controller 18 changes the parameter corresponding to the additional routine Rna read in Step S43 with the read modified parameter.

After execution of Step S45 or when the modified parameters are not reflected (Step S44; NO), the process proceeds to Step S46. Steps S46 to S52 correspond to Steps S32 to S382 of the routine R1 examination process in FIG. 5, to which the routine Rna is applied. The additional routine examination process ends.

Back in FIG. 4, after execution of Step S25 or when there is no additional examination input (Step S24; NO), the process proceeds to Step S26. The controller 18 determines whether or not to end the examination process for the routine set, depending on whether or not there is any routine of which an examination is not yet performed in the selected routine set (Step S26). That is, when the variable n is the number of routines in the routine set, the examination process of the routine set is completed. When the routine set examination process is to be completed (Step S26; YES), the routine set examination process ends.

If the examination process of the routine set is not to be completed (Step S26; NO), the controller 18 increments the variable n by +1 (Step S27). The controller 18 executes the routine Rn examination process for examining the n-th routine Rn in the execution order (Step S28). The process proceeds to Step S24. Here, the routine Rn examination process of Step S28 will be described with reference to FIG. 7.

The controller 18 reads, from the storage 19, the routine information and the reference image data of the routine Rn that is the n-th in the execution order (Step S61). After execution of Step S61, the process proceeds to Step S62. Steps S62 to S70 correspond to Steps S44 to S52 of the additional routine examination process in FIG. 6, to which the routine Rn is applied. The routine Rn examination process ends.

Next, specific examples of the routine examination process will be described with reference to FIGS. 11 to 12B. First, a first example of the routine examination process in a case where there is a modified parameter will be described with reference to FIG. 11. In the first example, the routine set examination process is executed and the routine set selected in Step S31 has the routines R1, R2, and R3 in the order of execution. The routine set examination process is a series of examinations performed on the same patient. In addition, the image mode of the routines R1, R2, and R3 is the B mode. Further, in the routine set examination process of the first example, the instruction to display the reference image data of each routine and the addition of a routine are not present.

First, the routine R1 examination process is executed in Step S23. In Step S35, there is an input of modification of a parameter. This modified parameter is referred to as a modified parameter P1. The modified parameter P1 indicates a small value of FOV because the physique of the patient to be examined is small. For the modified parameter P1, it is preferable to reduce the FOV also in the subsequent routines. In addition, for example, a modified parameter that decreases the gain may be used in a case where echo is less attenuated and is easily rendered because of a small physique of a patient. Also in the subsequent routines, it is appropriate to lower the gain.

In Step S37, the subject is imaged in the B-mode on the basis of various parameters of the routine R1 including the modified parameter P1. In Step S38, the routine information of the routine R1, the modified parameter P1, and the B-mode image data are stored.

After execution of the routine R1 examination process, the routine R2 examination process is executed in Step S28. In Step S62, there is the modified parameter P1 of the upstream routine R1. Therefore, in Step S63, the parameter of the routine R2 is changed by the modified parameter P1. In Step S69, the subject is imaged in the B-mode on the basis of various parameters of the routine R2 including the modified parameter P1. In Step S70, the routine information of the routine R2 and the B-mode image data are saved.

After execution of routine R2 examination process, the routine R3 examination process is executed in Step S28. In Step S62, since there is the modified parameter P1 of the upstream routine R1, the parameter of the routine R3 is changed by the modified parameter P1 in Step S63. In Step S69, the subject is imaged in the B-mode on the basis of various parameters of the routine R3 including the modified parameter P1. In Step S70, the routine information of the routine R3 and the B-mode image data are saved. The routine examination process ends.

Figure 12A:
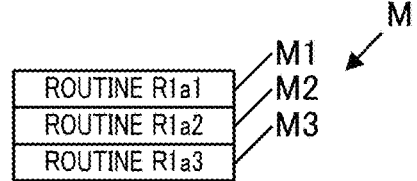
FIG. 12A shows an additional routine selection menu field.
Figure 12B:
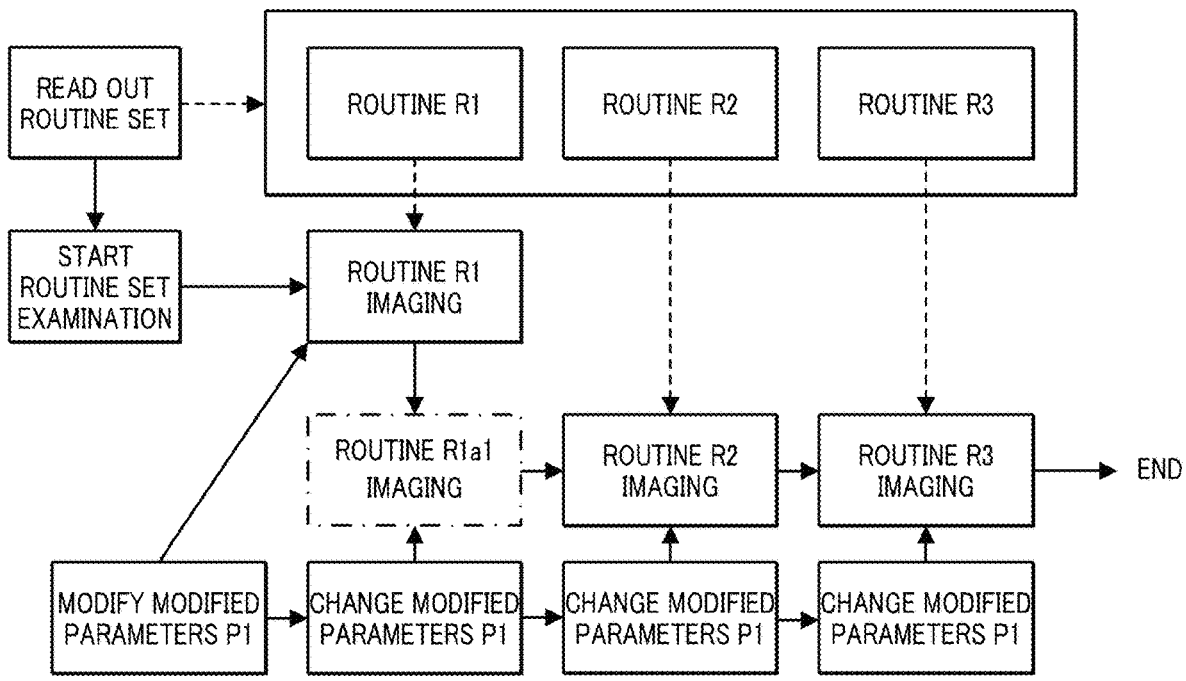
FIG. 12B shows an example of a routine set, parameter change, and routine addition.

With reference to FIGS. 12A and 12B, a second example of the routine examination process in a case where there is a modified parameter and there is an additional routine will be described. As shown in FIG. 12B, the routine set examination process is executed in the second example. The routine set selected in Step S31 includes routines R1, R2, and R3 in the order of execution. In addition, the image mode of the routines R1, R2, and R3 is the B mode. In addition, in the routine set examination process of the second example, there is no instruction to display the reference image data of each routine.

First, the routine R1 examination process is executed in Step S23. In step S35, there is an input of modification of a parameter. This modified parameter is referred to as a modified parameter P1. Since the physique of the patient to be examined is small, the modified parameter P1 is a smaller value of the FOV. In Step S37, the subject is imaged in the B-mode on the basis of various parameters of the routine R1 including the modified parameter P1. In Step S38, the routine information of the routine R1, the modified parameter P1, and the B-mode image data are stored.

After execution of the routine R1 examination process, an additional examination is input in Step S24. In Step S25, the additional routine examination process is executed. In Step S41, an additional routine selection menu field M shown in FIG. 12A is displayed. In the additional routine selection menu field M, selectable additional routines R1a1, R1a2, and R1a3 other than the routines R1, R2, and R3 can be selected and input. Here, the additional routine R1a1 is selected and input in Step S42.

At this time, in Step S44, there is a modified parameter P1 of the upstream routine R1. Therefore, in Step S45, the parameter of the additional routine R1a1 is changed by the modified parameter P1. In Step S51, the subject is imaged in the B-mode on the basis of the various parameters of the additional routine Rna1 including the modified parameter P1. In Step S52, the routine information of the additional routine Rna1 and the B-mode image are saved.

After execution of the additional routine Rna1 examination process, the routine R2 examination process is executed in Step S28. At this time, in Step S62, there is the modified parameter P1 of the upstream routine R1. Therefore, in Step S63, the parameter of the routine R2 is changed by the modified parameter P1. In Step S69, the subject is imaged in the B-mode on the basis of various parameters of the routine R2 including the modified parameter P1. In Step S70, the routine information of the routine R2 and the B-mode image data are saved.

After execution of the routine R2 examination process, the routine R3 examination process is executed in Step S28. In Step S62, there is the modified parameter P1 of the upstream routine R1. Therefore, in Step S63, the parameter of the routine R3 is changed by the modified parameter P1. In Step S69, the subject is imaged in the B-mode on the basis of various parameters of the routine R3 including the modified parameter P1. In Step S70, the routine information of the routine R3 and the B-mode image data are saved. The routine examination process ends.

As described hereinbefore, according to the present embodiment, the ultrasound diagnostic apparatus 100 includes the controller 18. The controller 18 sequentially performs ultrasonic imaging of the patient to be examined in a series of routines in order based on the information of the routine set by the control of the imager 101. The imager 101 generates ultrasonic image data by performing ultrasonic imaging on the subject of the patient. The routine set includes a plurality of routines for performing ultrasonic imaging using parameters. In a case where a parameter of an arbitrary routine is modified, the controller 18 changes a parameter of a routine on the downstream of the arbitrary routine by the modified parameter.

Therefore, it is possible to perform examinations of ultrasonic imaging using the routine set as a template. In the examinations of ultrasonic imaging using the routine set, the setting and modification of the parameters can be minimized, and the burden of setting the parameters on the examiner can be reduced. In particular, even in a routine on the downstream of the arbitrary routine, an examination can be started with satisfactory, if not optimum, modified parameters.

The information of the routine set corresponds to a plurality of routines for a patient(s) who has been imaged in the past. In the information (routine information and reference image data) in the routine set, the personal information of the patient who has been imaged in the past is deleted. Therefore, it is possible to easily reuse the information of the routine set without caring about personal information which is sensitive information of the patient who has been imaged in the past. For example, when the information of the routine set is displayed, it is possible to protect privacy by preventing the display of the personal information of the patient who has been imaged in the past.

The information of the routine set includes ultrasonic image data of a patient(s) acquired in the past of each routine. At the time of ultrasonic imaging of each routine in the routine set, the controller 18 displays ultrasonic image data of the patient imaged in the past of each routine on the display part 17. Therefore, by viewing the reference image, the examiner can stabilize the angle of manipulation, the angle of view, and the like of the ultrasonic image data of the patient under examination.

The controller 18 displays a key group K as operation elements on the display part 17. The key group K receives a user operation for transition to display processing of a captured ultrasonic image of a patient to be examined by the upward key K1. The key group K accepts a user operation for transition to modification processing of a parameter of an arbitrary routine by the down direction key K4. Therefore, it is possible to easily perform, with a user interface (UI), a transition to processing for displaying captured ultrasonic image data and a transition to processing for modifying a parameter of an arbitrary routine in the routine set examination.

The controller 18 receives an operation of adding a new additional routine to the routines of the routine set, and performs ultrasonic imaging of the additional routine by the control of the imager 101. Therefore, it is possible to easily add a new additional routine to the routine set and perform ultrasonic imaging.

The controller 18 displays, on the display part 17, the click key K5 of the key group K as the second operation element for receiving a transition operation to processing of a new routine addition. Therefore, the transition to the addition processing of a new additional routine can be easily operated using the UI.

In the above description, an example in which the ROM of the controller 18 is used as a computer-readable medium of the program according to the present invention is disclosed, but the present invention is not limited to this example. As other computer-readable media, a nonvolatile memory, such as a flash memory, and a portable recording medium, such as a CD-ROM, can be applied. Furthermore, a carrier wave is also applied as a medium for providing data of a program according to the present invention via a communication line.

Note that the description in the above embodiments is an example of the ultrasound diagnostic apparatus, the ultrasonic imaging method, and the storage medium according to the present invention. However, the present invention is not limited to the above embodiments.

Figure 13:
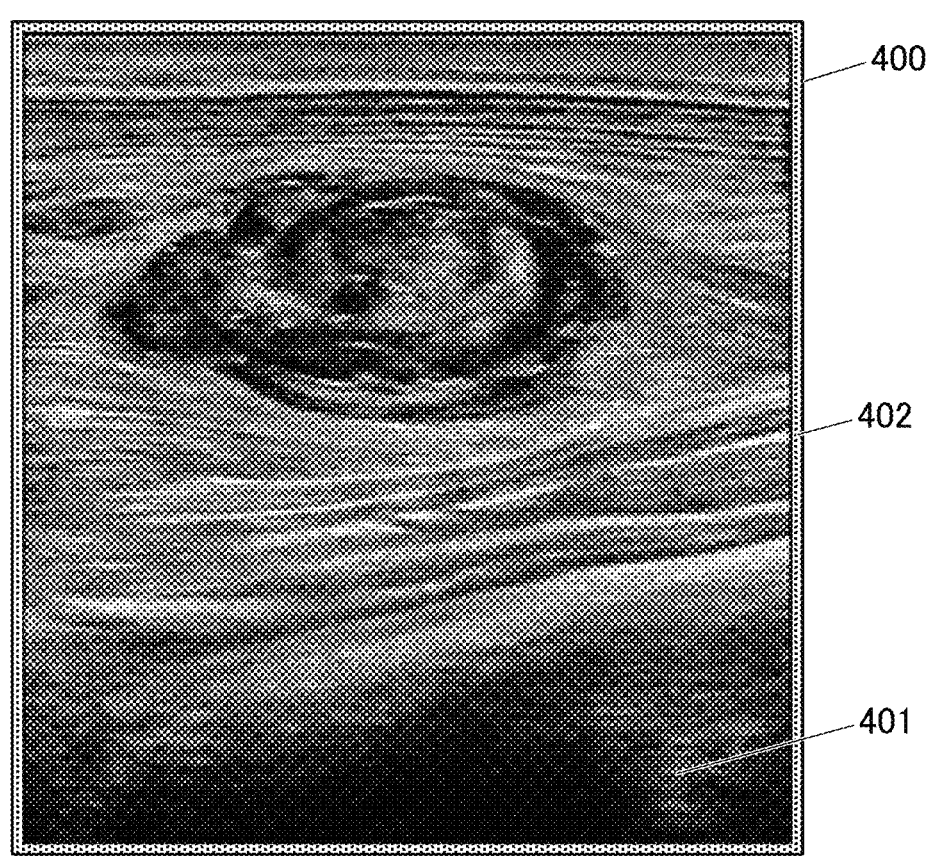
FIG. 13 shows a past ultrasonic image.

In the above-described embodiment, in the routine set examination process, the reference image data of a patient examined in the past or another patient is displayed in a mode in which the reference image data can be identified from the ultrasonic image under examination. For example, the ultrasonic image 300 during examination in FIG. 10, which is different from the ultrasonic image 200 during examination in FIG. 9, is displayed as a reference image. However, the present invention is not limited to this configuration. For example, in Steps S34, S48, and S66 of the routine set examination process, the reference image of the patient under examination and the reference image(s) of the other patient(s) may be displayed in a distinguishable manner. For example, a past ultrasonic image of a patient other than the patient under examination is displayed in the same display mode as the ultrasonic image 300 in FIG. 10. The ultrasonic image in the past of the patient currently under examination is displayed in a similar display mode to the ultrasonic image 400 of FIG. 13. FIG. 13 shows a past ultrasonic image 400.

In this configuration, the personal information is not deleted from the routine information of the routine set and the ultrasonic image data. The controller 18 determines, for example, based on the personal information, whether the subject in the past reference image is the patient under examination or another patient. When the subject of the past reference image is a patient other than the patient to be examined, the controller 18 displays the ultrasonic image 300 as the reference image on the display part 17. When the subject of the past reference image is the patient to be examined, the controller 18 displays the ultrasonic image 400 as the reference image on the display part 17. The ultrasonic image 400 includes an ultrasonic image main body 401 and a frame 402. The frame 402 is, for example, a green frame arranged around the ultrasonic image main body 401 in order to distinguish the ultrasonic image 400 from the ultrasonic images 200 and 300. However, the display mode for identifying the ultrasonic image 400 from the ultrasonic images 200 and 300 is not limited to the frame 402. For example, as a display mode, green characters "reference image" may be placed in the vicinity of the ultrasound image main body 401. The color of the display mode is not limited to green. For example, the controller 18 does not display, on the display part 17, personal information other than the frames 302 and 402 regarding the routine information and the ultrasonic image data of the patient who is the subject of the past reference image.

The controller 18 displays the captured ultrasonic image data on the display part 17 in different display modes depending on whether the imaged patient is the patient to be examined or a patient other than the patient to be examined. Therefore, it is possible to accurately and easily determine the patient (the patient to be examined (under examination) or another patient) of the subject of the reference image data, and to prevent an examination error.

In addition, the detailed configuration and the detailed operation of the ultrasound diagnostic apparatus 100 in the present embodiment described above can be appropriately modified without departing from the spirit and scope of the present invention.

The invention claimed is:

1. An ultrasound diagnostic apparatus comprising:
a hardware processor,
wherein the hardware processor is configured to sequentially perform ultrasonic imaging of a first patient in each of a plurality of routines by controlling an imager to generate ultrasonic image data, by ultrasonic imaging of the first patient based on information on a routine set including the plurality of routines of ultrasound imaging using a parameter, and
wherein the hardware processor is configured such that, when a parameter of a selected one of the plurality of routines is modified, the hardware processor changes a parameter of one or more routines downstream of the selected one of the plurality of routines according to the modified parameter, wherein the parameter of the selected one of the plurality of routines and the parameter of the one or more routines downstream of the selected one of the plurality of routines are common to each other.

2. The ultrasound diagnostic apparatus according to claim 1,
wherein the information on the routine set corresponds to a plurality of routines for a second patient who has been imaged.

3. The ultrasound diagnostic apparatus according to claim 2,
wherein personal information of the second patient is deleted from the information of the routine set.

4. The ultrasound diagnostic apparatus according to claim 2,
wherein the information of the routine set includes ultrasonic image data of the second patient that has been acquired before in each routine;
wherein, at a time of the ultrasonic imaging in each routine of the routine set, the hardware processor is configured to display, on a display part, the ultrasonic image data of the second patient that has been acquired before in each routine.

5. The ultrasound diagnostic apparatus according to claim 4,
wherein the hardware processor is configured to display the ultrasonic image data that has been acquired before on the display part in a different manner depending on whether the second patient is the first patient or a patient different from the first patient.

6. The ultrasound diagnostic apparatus according to claim 4,
wherein the hardware processor is configured to display on the display part a first operation element to accept a user operation for transition to display processing of the ultrasound image data of the second patient that has been acquired before or modification processing of the parameter of the selected one of the plurality of routines.

7. The ultrasound diagnostic apparatus according to claim 1,
wherein the hardware processor is configured to accept a user operation for addition of a new routine to the plurality of routines in the routine set and to perform ultrasound imaging in the new routine by controlling the imager.

8. The ultrasound diagnostic apparatus according to claim 7,
wherein the hardware processor is configured to display on a display part a second operation element to accept a user operation for transition to the addition processing of the new routine.

9. The ultrasound diagnostic apparatus according to claim 1,
wherein the hardware process is configured such that, when the parameter of the selected one of the plurality of routines is modified, the hardware processor changes the parameter of the one or more routines downstream of the selected one of the plurality of routines to the modified parameter.

10. An ultrasonic imaging method comprising:
sequentially performing ultrasonic imaging of a first patient in each of a plurality of routines by control of an imager which generates ultrasonic image data by the ultrasonic imaging of the first patient based on information on a routine set including the plurality of routines of ultrasound imaging using a parameter; and
changing, when a parameter of a selected one of the plurality of routines is modified, a parameter of one or more routines downstream of the selected one of the plurality of routines according to the modified parameter, wherein the parameter of the selected one of the plurality of routines and the parameter of the one or more routines downstream of the selected one of the plurality of routines are common to each other.

11. The ultrasonic imaging method according to claim 10, comprising:
when the parameter of the selected one of the plurality of routines is modified, changing the parameter of the one or more routines downstream of the selected one of the plurality of routines to the modified parameter.

12. A non-transitory storage medium storing a program that, when executed by a computer, is configured to cause the computer to:
sequentially perform ultrasonic imaging of a first patient in each of a plurality of routines by control of an imager which generates ultrasonic image data by the ultrasonic imaging of a subject of a patient based on information on a routine set including the plurality of routines of ultrasound imaging using a parameter; and
change, when a parameter of a selected one of the plurality of routines is modified, a parameter of one or more routines downstream of the selected one of the plurality of routines according to the modified parameter, wherein the parameter of the selected one of the plurality of routines and the parameter of the one or more routines downstream of the selected one of the plurality of routines are common to each other.

13. The non-transitory storage medium according to claim 12, wherein the program, when executed by the computer, is configured to cause the computer to:
change, when the parameter of the selected one of the plurality of routines is modified, the parameter of the one or more routines downstream of the selected one of the plurality of routines to the modified parameter.

* * * * *